United States Patent
Carruth et al.

(10) Patent No.: US 8,857,463 B1
(45) Date of Patent: Oct. 14, 2014

(54) MONITOR FOR PRESSURIZED CANISTERS

(75) Inventors: James B. Carruth, Panama City Beach, FL (US); James I. Fulton, Panama City Beach, FL (US); Christopher B. Bottomy, Panama City, FL (US); Thomas M. Hosea, Lynn Haven, FL (US); Marshal J. Black, Lynn Haven, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 250 days.

(21) Appl. No.: 13/440,723

(22) Filed: Apr. 5, 2012

(51) Int. Cl.
*F16K 21/10* (2006.01)
*F16K 21/04* (2006.01)
*G01N 7/00* (2006.01)
*G01N 9/00* (2006.01)

(52) U.S. Cl.
USPC ........ 137/514.7; 137/512.15; 137/9; 73/23.2; 73/23.24; 73/23.27; 73/31.04

(58) Field of Classification Search
None
See application file for complete search history.

(56) References Cited

U.S. PATENT DOCUMENTS

| 4,300,593 | A | * | 11/1981 | Ritter | 137/512.15 |
| 4,531,542 | A | * | 7/1985 | Looney | 137/514.7 |
| 5,904,170 | A | * | 5/1999 | Harvey et al. | 137/9 |
| 2010/0197035 | A1 | * | 8/2010 | Park et al. | 436/133 |

* cited by examiner

*Primary Examiner* — Andre Allen
(74) *Attorney, Agent, or Firm* — James T. Shepherd

(57) ABSTRACT

A sensor system is provided for pressure vessels. In one embodiment, a compressor directs compressed air into a purification chamber for removing carbon monoxide from the air. A sensor system housing is fastened to an opening on the purification chamber. The sensor housing provides an electrochemical sensor driven by an independent power supply and an electronic processor for receiving a signal from the electrochemical sensor. If the carbon monoxide in the purification chamber reaches a predetermined level, the electronic processor is programmed to initiate a shutdown of the compressor utilizing a relay cable.

8 Claims, 2 Drawing Sheets

MONITOR FOR PRESSURIZED CANISTERS

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

None.

BACKGROUND OF THE INVENTION (1) Field of the Invention

The present invention relates generally to monitoring pressurized containers and, in one possible embodiment, relates to a threadably connected real time carbon monoxide monitor that can be utilized to monitor a pressurized purification chamber, which requires maintaining a relatively high minimum pressure even when a compressor is turned off.

(2) Description of the Prior Art

Presently, carbon monoxide monitoring of compressed air systems may utilize carbon monoxide test strips, which may be placed inside a housing and exposed to compressed air. The test strips begin as a tan color and will change to black if carbon monoxide is present in undesired concentrations.

Draeger tubes provide another testing mechanism, which may be utilized in addition to other testing at regular intervals to independently gauge the quality of the compressed air for use in compressed air tanks.

The following U.S. Patents describe various prior art systems that may be related to the above and/or other carbon monoxide monitoring systems:

U.S. Pat. No. 6,433,696, to Dieterman et al., issued Aug. 13, 2002, discloses a system for monitoring carbon monoxide in an environment which includes an apparatus emitting carbon monoxide, such as an internal combustion engine. A carbon monoxide sensor measures a concentration of carbon monoxide in the environment and provides an electrical signal to a processor that is representative of the measured concentration of carbon monoxide. The processor determines the concentration of carbon monoxide corresponding to the electrical signal, provides an output signal at or above predetermined carbon monoxide concentration thresholds, calculates an estimated carboxyhemoglobin level for the operator corresponding to the carbon monoxide concentrations calculated over time, and provides an output signal at or above predetermined carboxyhemoglobin thresholds. The signals are then received by one or more devices which provide textual, visual, and/or audible warnings indicating that environmental concentrations of carbon monoxide have caused a predetermined warning threshold to be met or exceeded. The signals may also be received by a device which shuts down the carbon monoxide generating apparatus.

U.S. Pat. No. 3,970,431, to Wise, issued Jul. 20, 1976, discloses an indicator of the presence and changes in the carbon monoxide content of the air. It operates by measuring the change in resistance of a silver oxide detector when exposed to carbon monoxide.

The prior art does not show the features of the present invention which in one embodiment comprises a readily connectable sensor housing for pressure vessels and/or compressor systems including a substantially continuous real time measurement of carbon monoxide levels. The sensor housing may be used with breathing air compressor systems that contain scrubbing units of a type that are preferably kept at relatively high minimum pressures. Accordingly, those of skill in the art will appreciate the present invention, which addresses the above discussed and other problems.

SUMMARY OF THE INVENTION

It is one possible object of the present invention to provide an improved carbon monoxide monitor for a breathing air compressor system.

Another possible object of the present invention is to provide a self-contained sensor system with processing capability and battery pack within an easily replaceable threaded cap.

Another possible, object of the invention is to provide a real time monitoring system that can detect contaminants in stored compressed gas whether the system is operating or in standby mode.

Another possible object of the invention is to provide a carbon monoxide monitor which negates the need for periodic tests of breathing air using Draeger Tubes.

Other objects and advantages of the present invention will become apparent from the following descriptions, taken in connection with the accompanying drawings, wherein, by way of illustration and example, an embodiment of the present invention is disclosed. However, it will be understood that the present invention is not limited to the above and/or other objects of the invention.

In accordance with one embodiment of the present invention, a mechanism is provided for monitoring the carbon monoxide levels of air in a breathing air compressor system and for automatically shutting down the system if carbon monoxide levels reach a predetermined threshold. In one embodiment, the present invention may comprise elements such as, but not restricted to, a sensor housing comprising an electrochemical sensor, an electronic processor, a power supply and/or battery, an automated shutoff mechanism, and a back pressure regulator.

In one possible embodiment, a motor powers a breathing air compressor. A purification chamber is operably connected to the compressor for receiving a volume of high pressure breathing air to be scrubbed of carbon monoxide. A typical maximum pressure may be in the range of about 5000 psi. However, the purification chamber may also require a minimum pressure, which may be in the range of about 3000 psi.

In one possible embodiment, a carbon monoxide monitor cap is threadably mounted to an opening or connection on the purification chamber. The cap may be cylindrical in shape and comprise threads which mate with threads on the inside of the purification chamber opening. In another embodiment, at least one seal is used around the threads for a tight seal with the purification chamber. However, other shapes and fastening means can be utilized. The carbon monoxide monitor cap is portable and readily replaceable. It may be battery powered.

The carbon monoxide monitor cap may comprise an electrochemical sensor which is operably connected to an electronic processor. Both the sensor and the processor are powered by an independent power supply located in the cap.

In one embodiment, a sample of air is introduced through a metered orifice in the sensor cap. The airflow may be substantially continuous and is directed to the sensor. The processor can be programmed to utilize the sensor signal to detect undesired levels of carbon monoxide or other contaminants. In one possible embodiment, the air flow is approximately 1-1.5 liters of air per minute to provide adequate exposure to the electrochemical sensor.

In another embodiment the carbon monoxide monitor cap also comprises a back pressure regulator. The regulator maintains a desired minimum pressure in the breathing air compressor system, which in certain embodiments may be 3000 psi.

In one embodiment, once the electrochemical sensor detects a predetermined level of carbon monoxide as determined by the processor, the processor produces an output to shut off a fuel solenoid, which disables the air compressor. In another embodiment, the processor may shut off a switch or relay regulating electricity to the compressor.

DETAILED DESCRIPTION OF THE INVENTION

The present invention provides, amongst other things, an improvement in the real time monitoring of carbon monoxide in a breathing air compressor system. While a particular embodiment involves monitoring carbon monoxide, the present invention is not limited to this embodiment. For example, one possible embodiment of the present invention provides an easily replaceable self-contained sensor system and processor, which may be utilized for monitoring various aspects of a pressurized system and/or a pressurized canister.

Figure 1:
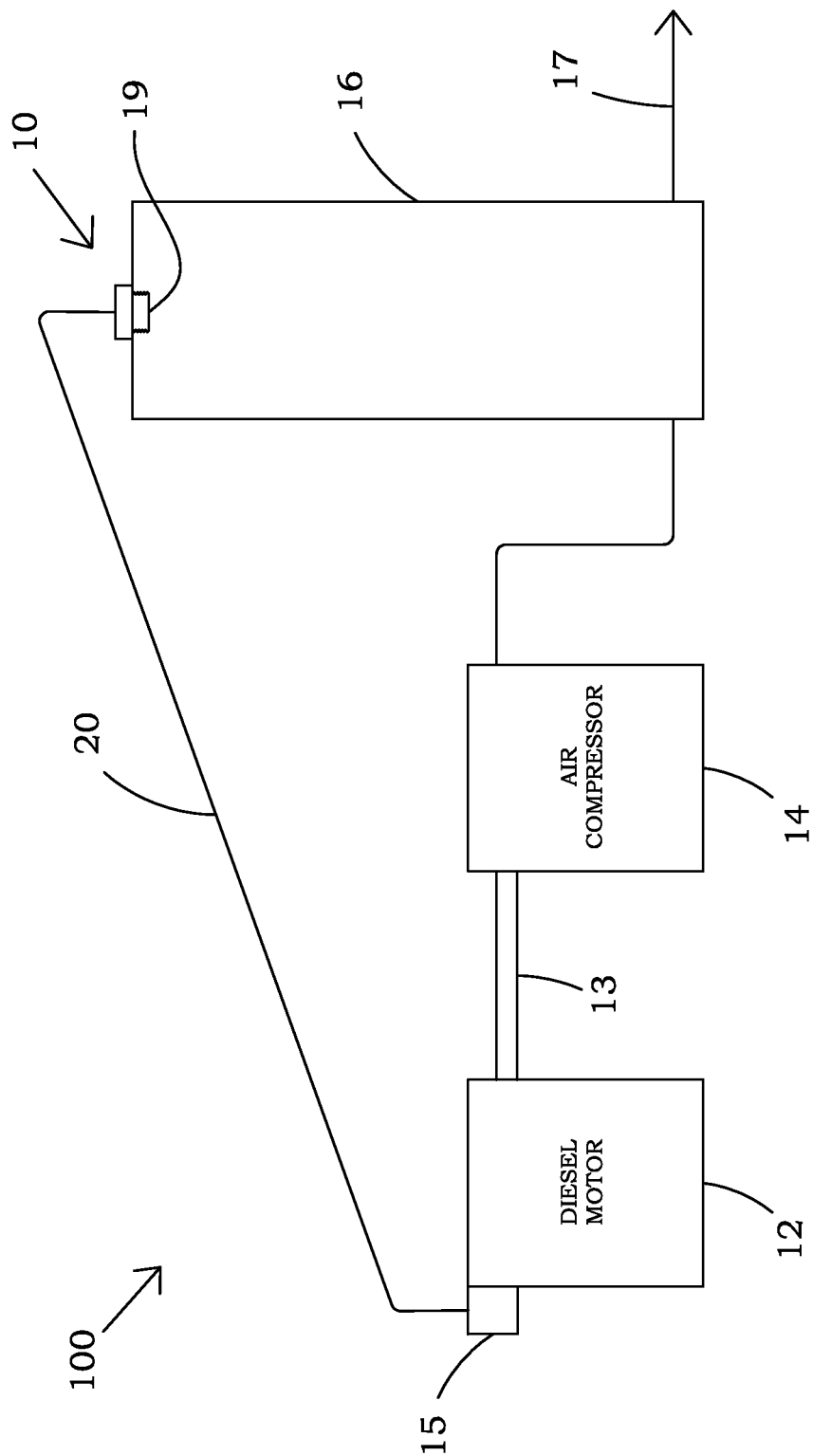
FIG. 1 is a schematic of a carbon monoxide monitoring system used in or as part of a breathing air compressor system that may include a purification chamber, scrubber, or the like in accord with one possible embodiment of the invention.

Referring now to the drawings and, more particularly to FIG. 1, there is shown one possible embodiment of air compressor system 100. System 100 may comprise a motor, such as diesel motor 12, which is utilized to drive air compressor 14 using some mechanical means such as pulleys, cranks, or in this embodiment, rotating shaft 13. However, motor 12 may comprise an electric motor, or any other suitable type of motor, and any suitable means may be provided to drive compressor 14. Motor 12 and compressor 14 may be integrated into a single unit. Accordingly, compressor 14 may be of various types and may be used to compress air for storage within one or more air chambers, such as purification chamber or compressed air chamber 16, as discussed hereinafter. However, compressor 14 may be utilized to compress other types of gases or combinations of gases as desired. Compressor system 100 may be provided as a package, may be transportable, and/or may be configured in many different ways. In one embodiment, compressor system 100 is utilized to compress air for breathing purposes, which may involve underwater use, firefighter use, medical use and/or other uses.

Shutoff 15 may be utilized to shut down motor 12 when the desired gas pressure is reached and/or if an undesirable level of carbon monoxide is detected, as discussed hereinafter. Shutoff 15 may comprise warning lights, electronic communication connections, and the like, which indicate problems with carbon monoxide levels. Shutoff 15 may also comprise a valve or the like to redirect the gas entering or leaving compressor 14.

In one embodiment, compressed air output line 17 may be utilized to connect with and/or charge other compressed air bottles as desired and/or for additional scrubbing.

Figure 2:
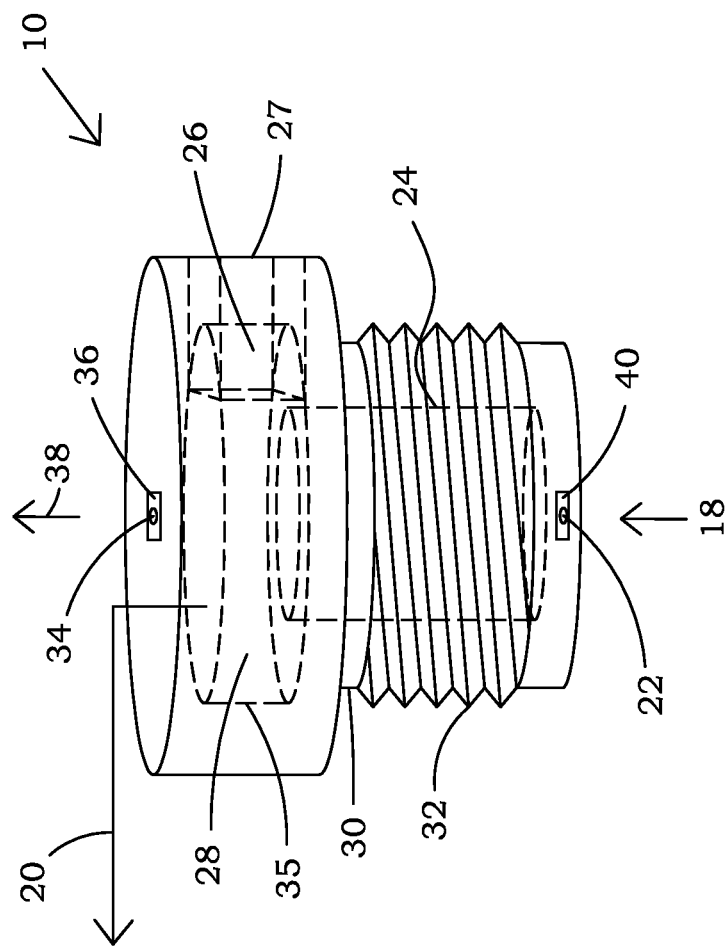
FIG. 2 is a perspective schematic view, partially in hidden lines, that shows a threaded sensor cap containing a sensor and processor for use with pressurized gas in accord with one possible embodiment of the invention.

Referring now to FIG. 2, there is shown one possible embodiment of a self-contained carbon monoxide sensor and processor for monitoring a breathing air compressor system. Sensor cap 10 is preferably portable, self-contained, and easily connected or removed from a high pressure cylinder, such as pressure vessel 16, when needed. In one possible embodiment, sensor cap 10 may be utilized in an air compressor system such as air compressor system 100 to detect undesirably high carbon monoxide levels.

In one possible embodiment, sensor cap 10 is designed to fit into opening 19 (See FIG. 1), which is provided or formed on pressure vessel 16. However, adaptors, valves, and the like may also be utilized for connecting sensor cap 10 to pressure vessel 16.

Pressure vessel 16 may be referred to herein as purification chamber, scrubber, air tank or the like. In one embodiment, pressure vessel 16 may comprise a carbon monoxide scrubber, filters, catalysts, or the like, which may preferably be maintained or may be required to be maintained at a minimum pressure. The minimum pressure may be relatively high, e.g., in the range of 3000 psi or the like. As used herein, the terms purification chamber, scrubber, and the like for removing carbon monoxide are substantially interchangeable. However, pressure vessel or chamber 16 may also comprise a standard compressed air cylinder.

In one possible embodiment, sensor cap 10 is cylindrically shaped and comprises threads 32 for connection to pressure chamber 16. However, other types of fittings, adaptors, seals, and connections could be utilized for sensor cap 10. Seals, such as seal 30, may comprise O-rings or other types of seals. Seals may be provided on both sides or one side of threads 32, as desired. In one embodiment, seal 30 may engage walls of corresponding socket 19 within pressure chamber 16, which provides a tight seal when sensor cap 10 is engaged with purification chamber 16.

Air flow into sensor cap 10, as indicated by arrow 18, enters through one or more orifices, such as metered input orifice 22 located on a lower end of cap 10, which is in communication with pressurized air in pressure chamber 16. Orifice 22 may be sized or metered to divert between 1-1.5 liters of air per minute, or other amount as desired, when connected to pressure chamber 16, which may have a maximum pressure in the range of about 5000 psi and, in one possible embodiment, a required minimum pressure in the range of about 3000 psi. The air that flows through metered input orifice 22 may then be directed through a flow path defined within sensor cap 10 and subsequently flow out of sensor cap 10 at output orifice 34 as indicated by arrow 38. The flow path within sensor 10 and one or more outputs, such as output orifice 34, may be sized considerably larger than input orifice 22, if desired. Output orifice 34 may be positioned as desired in sensor cap 10.

Referring to the details of FIG. 2, in one possible embodiment, sensor cap 10 forms internal housing 35 therein for various types of electrical and mechanical structures including metered input orifice 22 and output orifice 34, discussed hereinbefore. In one embodiment, the flow path within cap 10 is directed to flow through or past carbon monoxide electronic sensor 24, which is mounted within the housing formed within cap 10. While various types of carbon monoxide sensors or other sensors may be utilized, in one possible embodiment, off the shelf electronic sensors may be utilized such as an EcoSure Transducer, which requires no calibration and has a two year life.

Carbon monoxide sensor 24 is electronically connected to electronic processor 28, which may also be mounted within the interior of cap 10. In one possible embodiment, both sensor 24 and processor 28 are powered by a battery that forms power supply 26, which can also be contained within housing 35. In one embodiment, a battery can be replaced or inserted into housing 35 via a port in the side of housing 35 such as port 27, which may or may not be sealingly plugged. However, in other embodiments, the top of cap 10 could be sealed and/or threadably removable or other access means may be provided to access internal housing 35. Power may also be provided externally, if desired. One or more LEDs, buttons, or the like, may be utilized for checking operation, and/or to provide status indications, if desired.

Sensor cap 10 may in one embodiment be connected to sample air in a portion of purification chamber 16 that has already been filtered, scrubbed, exposed to catalyst of filter materials, or otherwise purified of carbon monoxide. As air is directed through sensor cap 10, carbon monoxide sensor 24 effectively samples and detects the amount of carbon monoxide present in the purification chamber. If the level of carbon monoxide becomes higher than a pre-set level as determined by a signal from sensor 24 and/or as calculated by processor 28, then electronic processor 28 may be programmed to or otherwise constructed to utilize wire 20 to activate shutoff 15, which may comprise a relay, fuel solenoid, or the like. As noted above, shutoff 15 may include warning lights, LEDs, or the like, which indicate the nature of the problem.

Sensor cap 10 may also include indicators such as a green LED for normal operation and/or a red LED for undesirable levels of carbon monoxide, which are controlled by processor 28.

Wire 20 may extend from an opening in sensor cap 10, which may be sealed by packing material, sealing material, or the like so as to provide that housing 35 remains pressurized, if desired. However, housing 35 may or may not be pressurized as desired, as discussed hereinafter.

In one possible embodiment with a diesel engine, processor 28 will transmit a shutoff signal to shutoff 15, which may comprise a fuel solenoid, via cable 20 preventing motor 12 from powering air compressor 14. In another embodiment utilizing an electric compressor, electronic processor 28 transmits a signal via cable 20 which connects to shutoff 15, which may comprise a mechanical relay or power transistor configuration that shuts off electric power for running air compressor 14.

As discussed above, air flow through internal housing 35 exits carbon monoxide monitor cap 10 through one or more openings, such as opening 34, which may be provided in the top of sensor housing 35, or at the sides, or elsewhere as desired.

In one possible embodiment, back pressure regulator 36 and/or back pressure regulator 40 may be utilized in conjunction with opening 34 or opening 18 to maintain a minimum pressure of 3000 psi in breathing air compressor system 100, although the minimum pressure could vary in other embodiments. For example, back pressure regulator 36 and/or 40 may comprise a check valve or the like which opens whenever the pressure goes above a minimum pressure, which may be in the range of about 3000 pounds. In one embodiment, the minimum pressure may be in the range of 3000 psi plus or minus 500 psi.

Housing 35 may or may not be pressurized. If back pressure regulator 40 operates in conjunction with input orifice 22, then housing 35 need not be pressurized. However, if it is desired that housing 35 be pressurized, then back pressure regulator 36 may be utilized in conjunction with outlet 34. If it is desired that housing 35 is pressurized, depending on the application, type of gas, and so forth, then housing 35 is appropriately sealed. Housing 35 may be vented to the atmosphere but could also be vented to a lower pressure line or container.

In either case, whether internal housing 35 is pressurized or not, sensor cap 10 may also be utilized to maintain a minimum system pressure within canister 16, if desired. In some cases, a minimum pressure may be desirable for proper maintenance or operation of purification or scrubbing chamber 16. With use of back pressure regulator 36 or 40, when gas pressure within purifier container is above a minimum level then gas will flow through housing 35 to contact sensor 24 at the predetermined flow due to metered orifice 22. However, in this embodiment, when pressure within gas canister 16 drops below the predetermined minimum, then flow through sensor cap no longer occurs. This is because if the pressure in pressurized chamber 16 drops below a minimum pressure, then back pressure regulator 40 will close and stop the flow to maintain the pressure in pressure chamber 16 at the minimum pressure, e.g. 3000 psi.

In summary of one possible embodiment of operation, compressor system 100 provides portable breathing air to be stored in canisters. In other embodiments, breathing air compressor system 100 could be used to directly deliver air to a breathing apparatus.

Motor 12 powers air compressor 14 to create a volume of pressurized air, which may increase in pressure up to about 5000 psi, depending on the application. The compressed air fills pressurized purification chamber 16 where carbon monoxide is scrubbed from the compressed air. In this embodiment, pressurized purification chamber 16 may be sealed off by sensor cap 10. If the carbon monoxide level of the compressed air is above a desired threshold, cable 20 sends a signal to shutoff 15, in the form of a fuel solenoid, preventing the delivery of fuel to diesel motor 12. In another embodiment, cable 20 carries a signal to shut off electrical power to electric air compressor 14. Purification chamber 16 also has one or more outlet ports 17 from which the breathing air reaches its ultimate destination, such as a scuba tank, compartment, medical oxygen tank, or other breathing apparatus.

In one embodiment, sensor cap 10 continuously checks air in pressurized purification vessel 16, so long as the system pressure is above a minimum pressure, and reduces the need to recalibrate carbon monoxide sensors or monitors. The carbon monoxide monitor also provides an automated shutoff mechanism based on a real time carbon monoxide reading and/or provides warning LED, signal, or the like.

In yet another embodiment, sensor cap 10 may not utilize wire 20 and might instead utilize LED indicators. Sensor cap 10 could then be connected to each air cylinder to be tested. The air in the tank could be sampled for a few minutes whereby the LED indicators would indicate whether unacceptable levels of carbon monoxide or other contaminants were present. Therefore, already filled bottles of gas may be tested for the presence of carbon monoxide and/or other elements. If a mixture of gases or ratio of gases were desired, then sensor cap 10 may comprise multiple sensors to test and measure the mixture, whereby processor 28 may produce an output from wire 20 and/or with a green LED.

While the present invention is discussed above for one embodiment, which utilizes a carbon monoxide sensor, other types of sensors may be utilized in addition or instead of the carbon monoxide sensor. Thus, sensor cap 10 of the present invention may be utilized for monitoring elements of different types in different types of gases and the signal output line may be utilized to connect to a shutoff but may also be utilized for other purposes such as signaling or monitoring purposes. Thus, sensor cap 10 may be used for other types of pressurized systems than compressed air systems and in some embodiments may not be utilized with air compressor systems but instead is used with testing gas in pressurized containers.

It will be understood that many additional changes in the details, materials, steps and arrangement of parts, which have been herein described and illustrated in order to explain the nature of the invention, may be made by those skilled in the art within the principle and scope of the invention as expressed in the appended claims.

The foregoing description of the preferred embodiments of the invention has been presented for purposes of illustration and description only. It is not intended to be exhaustive or to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A pressure chamber sensor for a pressurized chamber of gas which contains gas at a gas pressure, said pressure chamber sensor comprising:
   a sensor cap threadably adapted for connection to said pressurized chamber, a housing defined within said sensor cap, said sensor cap further defining an input orifice, in communication with said housing, and at least one outlet in communication with said housing, wherein said input orifice is sized to allow a predetermined flow of said gas through said input orifice, and wherein said housing is configured to direct said predetermined flow of said gas through said housing and out said at least one outlet;
   an electronic sensor mounted within said housing, said electronic sensor being positioned within said housing to encounter said predetermined flow of said gas through said housing;
   a back pressure regulator disposed in said sensor cap, said back pressure regulator being operable to allow said predetermined flow of gas to flow through said housing when said gas pressure is above a predetermined minimum pressure, said back pressure regulator being operable to prevent air flow through housing when said gas pressure drops below a minimum pressure.

2. The pressure chamber sensor of claim 1, further comprising an output line extending from said sensor cap, said output line being operable to transmit a signal responsive to said electronic sensor.

3. The pressure chamber sensor of claim 2, further comprising a processor mounted in said housing, said processor being interconnected to said sensor.

4. The pressure chamber sensor of claim 3, wherein said electronic sensor comprises a carbon monoxide sensor, and wherein said processor is programmed to produce said signal on said output line when a level of carbon monoxide detected by said sensor reaches a threshold level.

5. The pressure chamber sensor of claim 3, wherein said signal on said output line is operable to control a motor.

6. The pressure chamber sensor of claim 3, further comprising a power supply for said processor mounted within said housing.

7. The pressure chamber sensor of claim 6, wherein said power supply comprises a battery.

8. The pressure chamber sensor of claim 7, wherein said sensor cap defines an opening for insertion of said battery into said housing.

* * * * *